United States Patent
Hearn (10) Patent No.: US 10,334,876 B2
(45) Date of Patent: *Jul. 2, 2019

(54) SYSTEM COMPRISING A SIMULATED CIGARETTE DEVICE AND A REFILL UNIT

(71) Applicant: Kind Consumer Limited, London (GB)

(72) Inventor: Alex Hearn, London (GB)

(73) Assignee: KIND CONSUMER LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/634,898

(22) Filed: Jun. 27, 2017

(65) Prior Publication Data

US 2017/0290368 A1    Oct. 12, 2017

Related U.S. Application Data (62) Division of application No. 14/701,774, filed on May 1, 2015, now Pat. No. 9,723,870, which is a division of application No. 12/665,294, filed as application No. PCT/GB2008/002175 on Jun. 25, 2008, now Pat. No. 9,022,039.

(30) Foreign Application Priority Data

Jun. 25, 2007    (GB) .................................. 0712305.2

(51) Int. Cl.

| | |
|---|---|
| *F17C 5/06* | (2006.01) |
| *A24F 47/00* | (2006.01) |
| *A61M 15/00* | (2006.01) |
| *A61M 15/06* | (2006.01) |

(Continued)

(52) U.S. Cl.
CPC ....... *A24F 47/002* (2013.01); *A61M 15/0073* (2014.02); *A61M 15/0093* (2014.02); *A61M 15/06* (2013.01); *A61M 16/20* (2013.01); *A61M 16/208* (2013.01); *F17C 5/06* (2013.01); *A61M 15/0091* (2013.01); *A61M 16/107* (2014.02); *A61M 2205/8225* (2013.01);

(Continued)

(58) Field of Classification Search
None
See application file for complete search history.

(56) References Cited

U.S. PATENT DOCUMENTS

| | | | |
|---|---|---|---|
| 3,045,671 | A | 7/1962 | Updegraff |
| 3,705,590 | A | 12/1972 | Rains |

(Continued)

FOREIGN PATENT DOCUMENTS

| | | | | |
|---|---|---|---|---|
| DE | 4030257 A1 | 4/1992 | | |
| DE | 10051792 A1 | * 5/2002 | ........... | A24F 47/002 |

(Continued)

*Primary Examiner* — Phu H Nguyen
(74) *Attorney, Agent, or Firm* — Patterson + Sheridan, LLP (57) ABSTRACT

A simulated smoking device (1) comprising a simulated cigarette having a substantially cylindrical cigarette-like shape and a refill device (2, 50) having a substantially cuboid housing with a cigarette pack-like shape containing refill gas (32, 59) for the simulated cigarette and having means for selectively retaining the simulated cigarette. The simulated cigarette may be retained wholly within the housing. It may be retained at a location different from the refill location. A dose counter may be provided to give a visual indication of the doses in the refill device.

6 Claims, 7 Drawing Sheets

(51) Int. Cl.
*A61M 16/10* (2006.01)
*A61M 16/20* (2006.01)

(52) U.S. Cl.
CPC ... *F17C 2201/056* (2013.01); *F17C 2221/011* (2013.01); *F17C 2221/03* (2013.01); *F17C 2270/02* (2013.01)

(56) References Cited

U.S. PATENT DOCUMENTS

| | | | |
|---|---|---|---|
| 3,721,240 | A | 3/1973 | Tamburri |
| 4,171,000 | A | 10/1979 | Uhle |
| 7,080,642 | B2 * | 7/2006 | Hodson ............. A61M 15/0045 |
| | | | 128/200.11 |
| 2004/0221840 | A1 | 11/2004 | Stockman-Lamb |
| 2006/0196515 | A1 | 9/2006 | Gomes |

FOREIGN PATENT DOCUMENTS

| | | |
|---|---|---|
| EP | 0684047 A2 | 11/1995 |
| JP | 0177399 | 5/1989 |
| WO | 0145768 A2 | 6/2001 |
| WO | 0180672 A1 | 11/2001 |

* cited by examiner

SYSTEM COMPRISING A SIMULATED CIGARETTE DEVICE AND A REFILL UNIT

CROSS-REFERENCE TO RELATED APPLICATIONS

This application is a divisional of U.S. patent application Ser. No. 14/701,774, filed May 1, 2015, which is a divisional of U.S. patent application Ser. No. 12/665,294, filed May 28, 2010, which is a national stage entry of International Application No. PCT/GB08/02175, filed Jun. 25, 2007, which claims benefit of U.K. Application No. 0712305.2, filed Jun. 25, 2007, which applications are hereby incorporated by reference in their entirety.

BACKGROUND OF THE INVENTION

Field of the Invention

The present invention relates to a system comprising a simulated cigarette device and a refill unit.

Description of the Related Art

It is estimated by the World Health Organisation that tobacco smoking kills 3-4 million people per year, and that the number of smokers in the world is rising per annum. Nicotine replacements therapies have become more widespread in Western Countries but still are not having as widespread effect in making smokers quit as many had predicted. Moreover many current and ex-smokers are unsatisfied with NRT, with 67% failing to give up because they find current NRT treatments impractical, unsatisfying or uncustomary (UK Government Statistics 2004). There is a growing need for a device which replicates the same habitual patterns of smoking, which smokers are used to, as well replicating the style and functionality of a cigarette and its pack. Moreover, it is increasingly becoming apparent that there is a need for a system which satisfies the taste and sensory needs of a smoker and a system which is able to deliver nicotine in an unmetered dosage, which a user can regulate according to his craving. One of the aims of the present invention therefore is to provide a non-carcinogenic cigarette capable of fulfilling the habitual as well as the physical cravings of smoking, which can be a socially acceptable form of nicotine replacement therapy. A further aim of the present invention is to provide a device and refill that is a more convenient, affordable and customary form of nicotine replacement therapy, which delivers faster acting nicotine and can be readily incorporated into existing tobacco retailing formats, especially in lieu of changing legislation which may outlaw the display of tobacco packs in retail outlets.

With the growing restrictions on the smoking of cigarettes in public places, there is room for a device which can replicate the physical act of smoking, which is socially acceptable such that it can be used in all public places. Also, there is a need for a device which can be used to dispense nicotine in a non-smokable form either as a cigarette replacement, or to address the nicotine dependency that smokers feel thereby helping them to give up smoking. Other gaseous substances such as oxygen may be dispensed as these are known to have beneficial effects in the process of nicotine substitution.

A number of simulated cigarette devices are known in the art, for example in U.S. Pat. Nos. 3,631,856, 3,721,240 and DE 4030257. All of these are refillable from a refill container.

WO 01/49349 discloses an oxygen delivery apparatus in which oxygen is stored in a canister which is then removed from the device and either refilled or replaced. Again, no indication is provided of how the refilling is carried out in practice.

U.S. Pat. No. 3,045,671 discloses a portable inhaler having a chamber which can be refilled by screwing a cartridge holder having a generally cylindrical capsule on to the end of the device which communicates with the chamber via a refill valve. The inhaler is intended to provide an emergency supply of oxygen for medical purposes and is not configured as a simulated cigarette device.

U.S. Pat. No. 4,171,000 discloses a simulated cigarette device having a chamber filled with a fibrous storage substance. A cylindrical pressure vessel containing a mixture to be inhaled is movable towards this chamber to dispense the material from the pressure vessel on to the storage substance allowing it to be inhaled by the user According to the present invention there is provided a simulated smoking device comprising a simulated cigarette having a substantially cylindrical cigarette-like shape and a refill device having a substantially cuboid housing with a cigarette pack-like shape containing refill gas for the simulated cigarette and having means for selectively retaining the simulated cigarette.

By configuring the simulated cigarette to resemble a cigarette and the refill device to resemble a cigarette pack, the present invention closely replicates the smoking experience. The cigarette user is therefore likely to be more comfortable purchasing a product that has the appearance of a cigarette and cigarette pack. Also, the invention allows them to replicate the ritual of removing the cigarette from the pack and inhaling from the cigarette. In also allows the user a refilling ritual which is similar in process, habit and operation as igniting a conventional tobacco cigarette with a lighter. The present invention is therefore more likely to gain acceptance from smokers as a credible smoking substitute and can also be readily adapted for sale in point-of-purchase retail channels that are customary for tobacco.

The refill housing preferably has a height of 44 to 176 mm a width of 21 mm to 112 mm and a depth of 8 to 60 mm. More preferably the height is 80 to 120 mm, width 20 to 60 mm and depth 15 to 30 mm. Optimally the height is 88 mm, the width is 56 mm and the depth is 24 mm to conform to a standard vending pack of twenty cigarettes.

The simulated cigarette device preferably comprises an elongate housing having an inhaling outlet at one end and a refill inlet, a reservoir extending along a substantial portion of the housing and having a refill valve adjacent to the refill inlet and an outlet valve adjacent to the inhaling outlet, which is operable to allow gas from the reservoir to pass from the reservoir and out of the inhaling outlet.

The refill device preferably comprises a gas reservoir having an outlet and an associated reservoir outlet valve, wherein the refill valve of the cigarette device is arranged to co-operate with the reservoir outlet valve to open a flow path from the reservoir of the refill to the reservoir of the cigarette device.

A combination of the device and refill unit can have sufficient capacity to last for a number of days, depending on patterns of use, of normal use before a refill unit needs to be refilled or replaced. The reservoir from which the refill unit itself is refilled could, for example, be a vending machine, or a higher pressure cylinder which the user can keep at home or in their car such that they do not have to carry it with them at all times. However, the current preference is to sell replacement refill units, rather than making them refillable.

The reservoir preferably has a volume of between 500 mm.sup.3 and 10,000 mm.sup.3, and more preferably between 2200 mm.sup.3 and 2600 mm.sup.3. A standard pressurized solution containing nicotine, solvent, propellant and oxygen is preferably at a pressure of 2-150 bar, more preferably at 5-20 bar and optimally at 6 bar. A solution containing a high percentage of oxygen is preferably at a pressure of between 5 and 150 bar and is more preferably at a pressure of between 20 to 25 bar.

The device can typically provide between 8 and 24 puffs before the reservoir requires refilling.

The refill unit preferably has a volume of between 10,000 mm.sup.3 and 100,000 mm.sup.3, and more preferably between 40,000 mm.sup.3 and 50,000 mm.sup.3. A standard refill solution is at a pressure of 2-150 bar, more preferably at 5-20 bar, and optimally at 6-8 bar. A solution containing a high percentage of oxygen is preferably at a pressure of between 5 and 150 bar and is more preferably at a pressure of between 20 to 30 bar.

The refill unit can typically provide between 80 and 1000 puffs and more preferably between 120 and 200 puffs before it requires refilling.

The composition preferably comprises oxygen, nicotine or a derivative or salt thereof, an antioxidant, an aroma and/or flavour component, a propellant and a solvent. It may also comprise a cognitive enhancing additive. Details of the composition are given in co-pending application GB 0712308.6

Additionally the reservoir can be provided with a manual pump such as a compression pump activated by a trigger or push-down button located on the top or the side refill pack much like the manual habit associated with a cigarette lighter. This serves to prime, regulate and re-pressurize the reservoir so a constant dose and pressure is maintained and delivered.

Preferably the refill unit is provided with a dose counter to register the number of times that the simulated cigarette is refilled and display this to a user. This gives a clear visual indication that a refill has run out of gas so that the user does not keep attempting to fill the simulated cigarette from an empty refill. Also, it allows the user to buy a new refill in plenty of time before the existing refill runs out of gas.

This forms an independent aspect of the present invention which may be defined in the broadest terms as a simulated smoking device comprising a simulated cigarette and a refill device containing refill gas for the simulated cigarette and having means for selectively retaining the simulated cigarette, the refill device further comprising a dose counter to register the number of times that the simulated cigarette is refilled and display this to a user.

The device may be configured such that the means for selectively retaining the simulated cigarette retains the cigarette in the refill position. However, preferably, the means for selectively retaining the simulated cigarette is arranged to retain the simulated cigarette in a position which is different from the position in which the simulated cigarette is refilled.

Separating the position in which the simulated cigarette is stored from the position in which it is refilled allows the designer freedom in the manner in which the cigarette is stored for ease of access, while at the same time allowing also the outlet from the refill device to be conveniently positioned. It also allows the experience of the real cigarette and pack to be more closely replicated.

This forms an independent aspect of the present invention which can be defined in the broadest sense as a smoking device comprising a simulated cigarette and a refill device containing refill gas for the simulated cigarette device and having means for selectively retaining the simulated cigarette arranged to retain the cigarette device in a position which is different from the position in which the simulated cigarette is refilled.

Preferably the means for selectively retaining the simulated cigarette is arranged to accommodate the simulated cigarette entirely within the housing.

Retaining the simulated cigarette entirely within the housing provides an arrangement which is much more akin to the traditional cigarette packet.

This forms an independent aspect of the present invention which can be defined in the broadest sense as a simulated smoking device comprising a simulated cigarette and a refill device having a housing containing refill gas for the simulated cigarette and having means for selectively retaining the simulated cigarette entirely within the housing.

The present invention also extends to a refill device for use with a simulated smoking device according to any one of the aspects of the invention described above.

Also, preferred features of one aspect of the invention apply equally to other aspects of the invention.

The refill unit may preferably comprise a single cylinder of gas, but can also comprise at least two cylinders as this allows more gas to be accommodated in packaging of a convenient size.

When two cylinders are provided, the cylinders may be entirely separate such that the user fills the cigarette device from one or the other. One may be accessible from the outside of the refill unit, and the other may be accessible from the inside. The cylinders may be in the same orientation, or may be inverted with respect to one another. However, preferably, there is provided a ducting and valve system such that the cigarette device is arranged to be filled simultaneously from both cylinders.

The refill unit may be provided with a first gas path through which the cigarette device is filled and a second gas path through which the refill unit is refilled. However, preferably, the cigarette device is filled through the same gas path that is used to refill the refill unit.

The cigarette device with oxygen forms the subject of co-pending applications GB 0712304.5 and 0712306.0

SUMMARY OF THE INVENTION

An example of a device and system in accordance with the present invention will now be described with reference to the accompanying drawings, in which:

Figure 4:
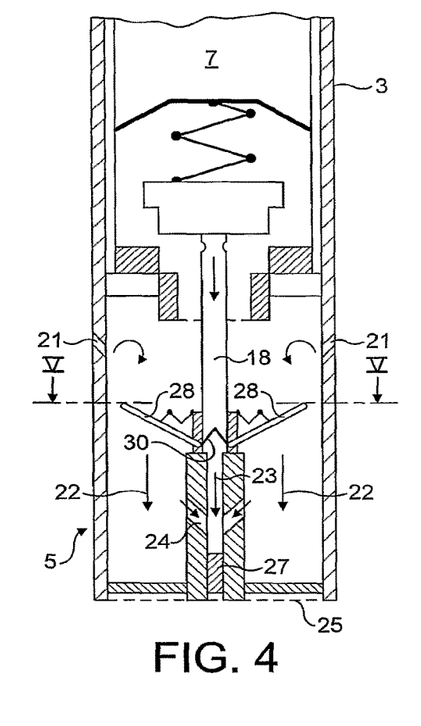
FIG. 4 is a view similar to FIG. 3 showing an alternative design of the breath activated valve.
Figure 5:
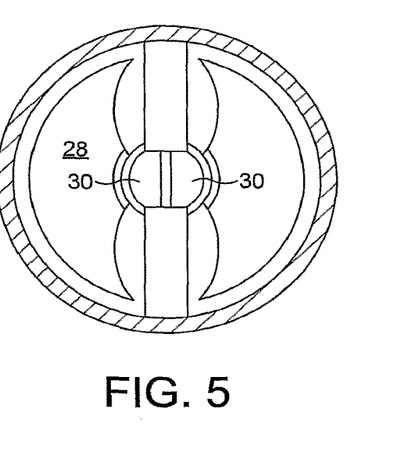
FIG. 5 is a cross-section through line V-V in FIG. 4.
Figure 6:
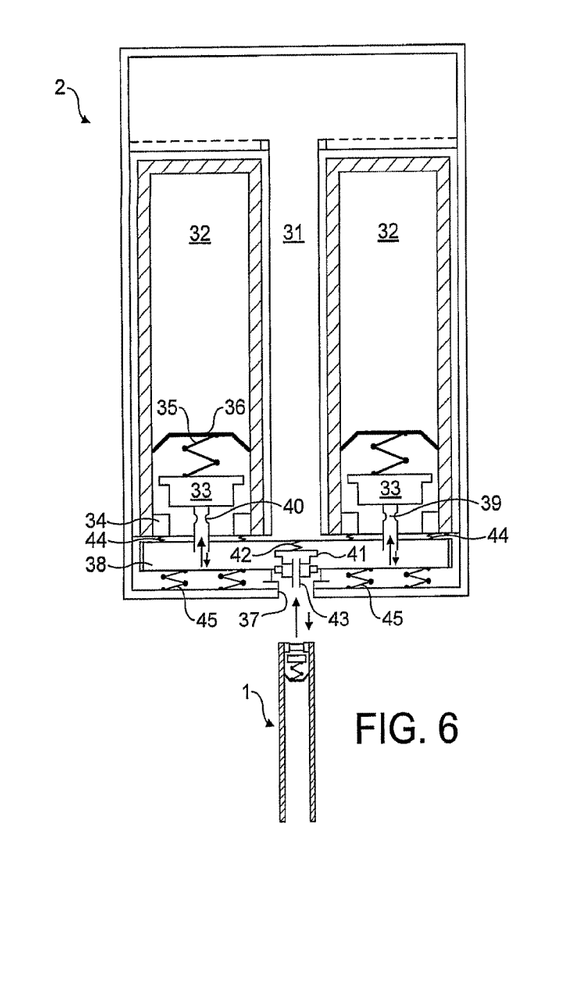
FIG. 6 is a schematic cross-section of a first refill unit.
Figure 7:
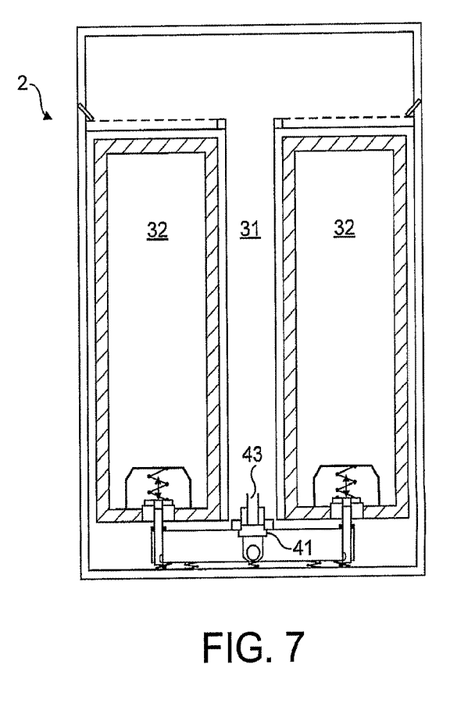
FIG. 7 is a schematic view similar to FIG. 6 of a second refill unit.
Figure 8:
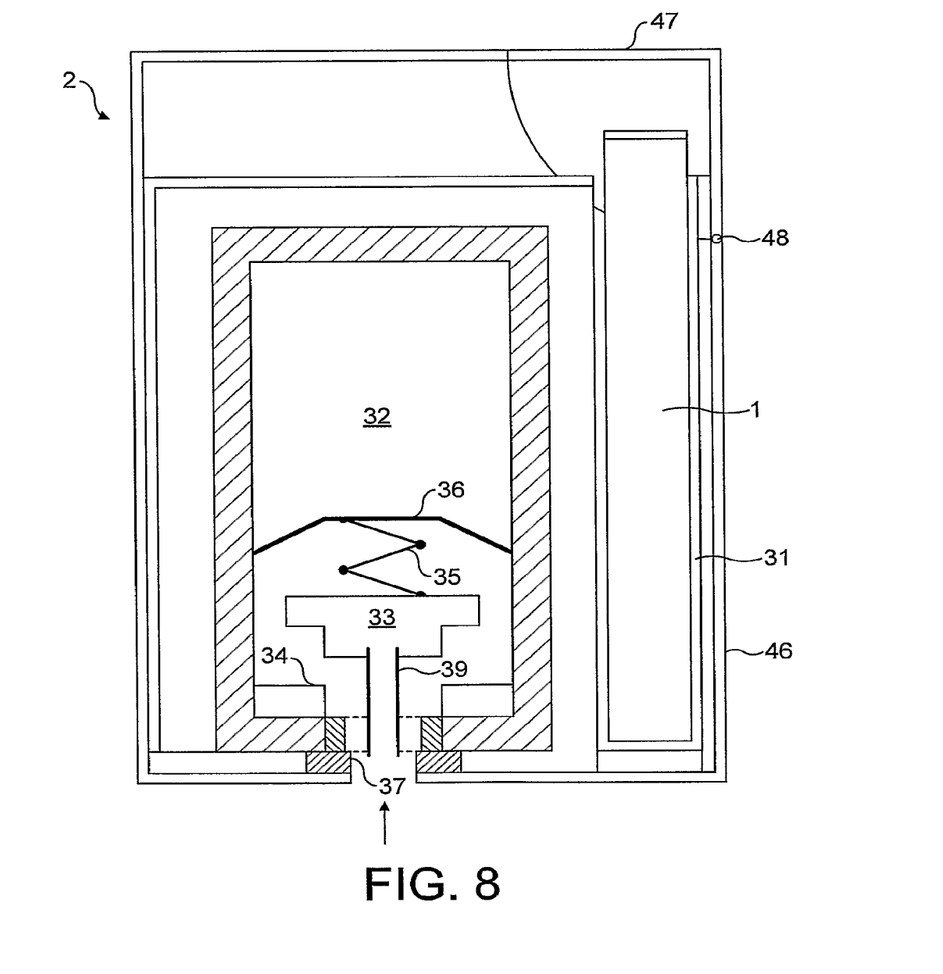
FIG. 8 is a schematic cross-section showing a third refill unit.

The system comprises two main components namely a simulated cigarette device 1 shown in FIGS. 1 to 5 and a refill unit 2 shown in FIGS. 6 to 8.

DETAILED DESCRIPTION

Figure 1:
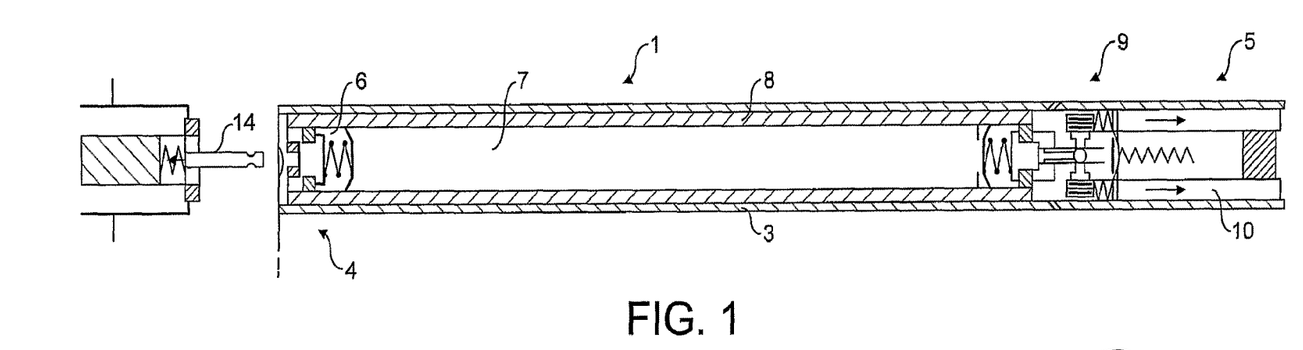
FIG. 1 is a schematic cross-section through the device also showing the refill nozzle.

The simulated cigarette device 1 will be described first. This comprises an elongate hollow cylindrical housing 3. One end of this housing is a refill end 4 and the opposite end is an inhaling end 5. At the refill end a check valve 6 is described in more detail below. This leads to a reservoir 7 which extends along a substantial portion of the length of the device. As shown in FIG. 1, the reservoir is defined by a cylindrical sleeve 8 tightly fitted within the cylindrical housing 3. It could, however, be defined by the cylindrical housing 3 itself. At the opposite end of the reservoir 7 to the refill end 4 some three quarters of the way along the device is a breath activated outlet valve 9 that is described in more detail below. This leads to an outlet at the inhaling end 5. The reservoir 7 is periodically filled with gas through the check valve 6. A user then sucks on the inhaling end 5 periodically opening the breath activated valve 9 to draw doses of the gas from the reservoir 7.

Figure 2A:
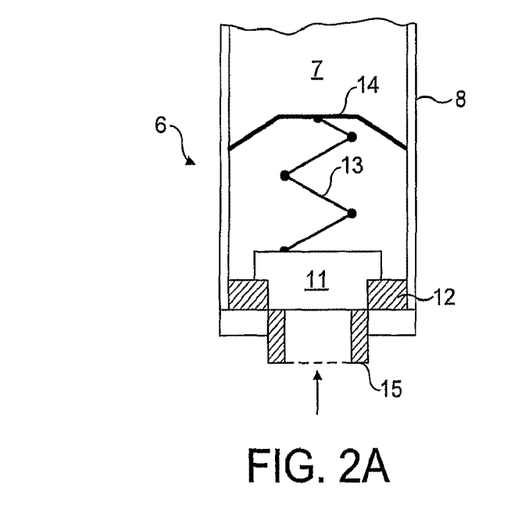
FIG. 2A is a schematic cross-section through a distal end of the device with a refill valve in the closed position.
Figure 2B:
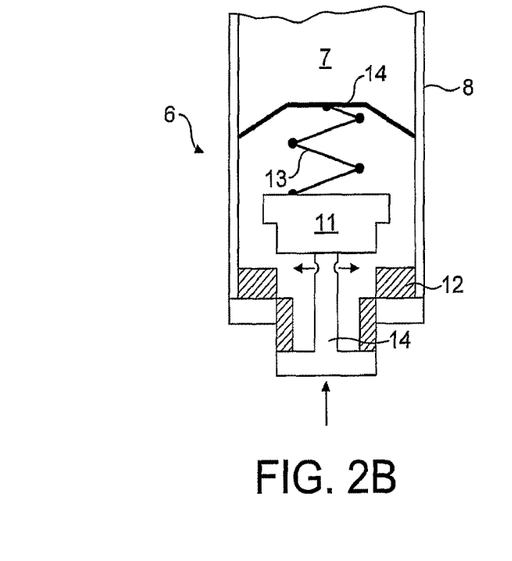
FIG. 2B is a view similar to FIG. 2a with the valve in the open position.

The check valve 6 will now be described in more detail with reference to FIGS. 2A and 2B. The check valve comprises a valve element 11 which is biased onto a valve seat 12 by a spring 13. The spring 13 is supported at its opposite end by a spring support 14 which is open to allow gas to pass. The refill end 4 also has a refill seat 15 upstream of the valve element 11. In order to refill the reservoir, a refill nozzle 14 is inserted into the refill end 4 of the device 1. The refill nozzle 14 pushes on valve 11 to lift it from its seat, while the end of the nozzle seals against nozzle seat 15 to seal the end of the reservoir during the refill processes. As shown in FIG. 1, the refill nozzle 14 is spring-loaded such that it automatically dispenses gas when pressed against the valve element 11. Alternatively, an independent gas release mechanism may be provided for the refill.

As the nozzle is withdrawn, the spring 13 pushes the valve element back onto its seat to seal the end of the reservoir.

The breath activated valve 9 will now be described with reference to FIG. 3. This comprises a valve element 16 in the form of an elongate rod with a through hole 17. This through hole 17 is positioned in a tubular outlet 18 leading to the reservoir 7. In the position shown in FIG. 3, the through hole 17 is perpendicular to the tubular outlet 18 thereby blocking flow through the tubular outlet 18. When the valve element 16 is rotated through 90 degrees the through hole 17 comes into alignment with the tubular outlet 18 allowing flow from the reservoir 7.

Figure 3:
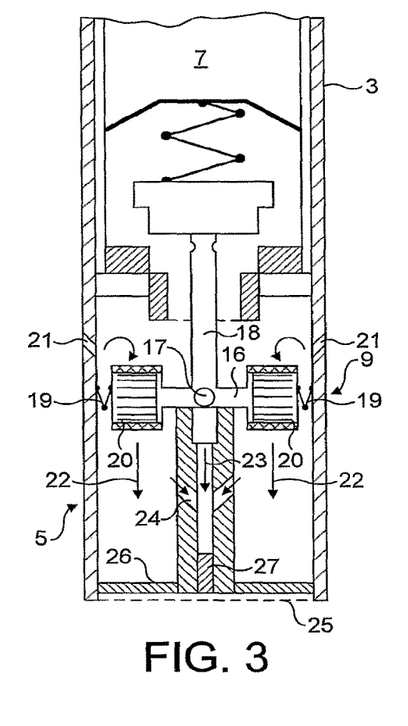
FIG. 3 is a schematic cross-section showing the breath activated valve at the proximal end.

The valve element 16 is held in the closed position shown in FIG. 3 by a pair of biasing springs 19. At either end of the valve element 16 is a vane system 20. Upstream of the vane system 20 are a pair of oblique inlets 21. These are positioned and oriented such that air flowing through the inlet impinges on the vane system 20 in such a way as to cause the valve element to rotate to the open position against the action of the biasing springs 19, thereby opening the valve. Thus, the valve is activated by a user sucking on the inhaling end of the device. When the sucking stops, the biasing springs 19 cause the valve to close.

As can be seen in FIG. 3, there are two streams flowing towards the inhaling end 5. These are the ambient air stream from the oblique inlets 21 designated by arrows 22 and the stream from the reservoir 7 which has passed through hole 17 as designated by reference numeral 23, a pair of bleed flow orifices 24 bleed a proportion of the ambient air stream 22 into the stream 23 and are directed obliquely so as to promote flow towards the inhaling end 5. This is done as the gas from the reservoir may be particularly cold and it is therefore diluted by the ambient air from streams 20. At the inhaling end is a screen 25 which holds in place an annular filter element 26 for the external flow passageway and a central filter element 27 for the flow from the reservoir. These prevent external debris from entering the device.

An alternative arrangement of breath activated valve will now be described with reference to FIGS. 4 and 5.

Most components of the inhaling end 5 are the same as those described previously and have been designated with the same reference numerals. Only the valve mechanism itself is different. This comprises a pair of plates 28 which are pivotally mounted and biased into the first position shown in FIG. 4 by a respective balancing spring 29. Extending generally perpendicular from each plate 28 are sealing elements 30. The sealing elements 30 are preferably made of a material with a degree of resilience such as an elastomer, or may be a rigid material with a resilient tip at the end to provide a seal. The seal element meets in the middle of the tubular outlet 18 to seal the flow path through the outlet. In the device, air from oblique inlets 21 impinges on plates 28 causing the plates to rotate downwardly from the position shown in FIG. 4 thereby parting the sealing elements 30 and allowing flow from the reservoir 7. When the suction stops, the plates 28 are urged back to the starting position shown in FIG. 4 and the tubular outlet 18 is sealed again.

A first example of the refill unit will now be described with reference to FIG. 6.

The refill unit is approximately the same size and shape as a cigarette packet. The unit has a substantially cuboid configuration. It will be understood that some departure from the strict cuboid shape can be accommodated, while still providing a substantially cuboid shape. For example, the edges may be rounded, or the unit may have a slightly curved configuration allowing it to fit more readily into a user's pocket. Such variations, among others, are considered to be within the requirements for a substantially cuboid cigarette pack-like shape. The refill unit is provided a recess 31 in which the cigarette device 1 can be stored when not in use. The refill unit comprises a pair of gas cylinders 32 positioned on either side of the recess 31.

Each cylinder 32 has the same construction. Each cylinder has an inlet/outlet valve comprising a valve element 33 which is biased onto a valve seat 34 by biasing spring 35 which is supported on spring support 36.

In order to fill the cigarette device 1 from the refill unit 2, and in order to refill the refill unit 2 itself, a ducting system is provided to provide a flow communication between an inlet/outlet 37 and the cylinders 32. This takes the form of a spring-loaded duct 38 which leads from the inlet/outlet 37 to the two cylinders 32. The duct is provided with a pair of nozzles 39 each of which is arranged to press against a respective valve element 33, and each of which is provided with a plurality of orifices 40 which allow flow communication between the internal space of the cylinder 32 and the spring loaded duct 38. Adjacent to the inlet/outlet 37 is a duct valve 41 normally biased into a closed position by spring 42. A duct nozzle 43 similar to the nozzle 39 is associated with valve 41.

In an unused configuration, the spring-loaded duct 38 is biased into a position closely adjacent to the bottom of the refill unit by a spring 44. At this time, the valve elements 33 are seated as is duct valve 41, each being biased into its closed position by a respective spring. When the cigarette device 1 is inserted in the inlet/outlet 37, the check valve 6 on the cigarette device 1 is opened as described above. The duct valve 41 is pushed into an open position, and the entire spring-loaded duct 38 is lifted to the position shown in FIG. 6 assisted by springs 45. This causes nozzle 37 to lift valve elements 33 from their seats. There is now flow communication from the cylinders 32 into the reservoir 7 of the cigarette device. As the gas cylinders 32 are at the higher pressure than the cigarette device, the air flows into the reservoir 7. Each cylinder 32 has a pressure of sufficient gas to refill the cigarette device 14 times.

When the cylinders 32 run low on gas, the refill unit may be disposed of, ideally for recycling, and replaced with a new unit. Alternatively, the cylinders may be refillable. This is done using the same mechanism as is used to refill the cigarette device from the cylinders. In order to do this, a high pressure gas source (not shown) is placed into the inlet/outlet 37 in the same way that the cigarette device is inserted and the same flow path is opened up. As the high pressure gas source is at a higher pressure than the cylinders 32, the cylinders are refilled. This is also the manner in which the cylinders 32 are filled for first use.

It is envisaged, for example, that the high pressure gas source may be provided as a vending machine such that the user may refill their gas cylinder from this, or may be a gas canister that a user keeps in their house or car.

FIG. 7 shows a second refill unit 2. This is similar to the first unit, but, in this case, is designed to refill the cigarette device when the cigarette device is in the recess 31. Thus, the duct valve 41 and duct nozzle 43 are inverted from their positions from FIG. 6 and corresponding adjustments are made to the rest of the mechanism. This allows the cigarette device 1 to be automatically refilled when placed in the refill unit.

A third refill unit is shown in FIG. 8. This unit comprises a casing 46 having a lid 47 which is hinged at hinge 48. When the lid is opened, the cigarette device 1 may be inserted into and removed from recess 31. The refill comprises a single cylinder 32 constructed in accordance with the cylinders described in relation to FIG. 6. As this example only has a single cylinder, the inlet/outlet 37 directly below the nozzle 39 such that the cigarette device 1 and high pressure gas source press directly on the valve element 33.

Figure 9A:
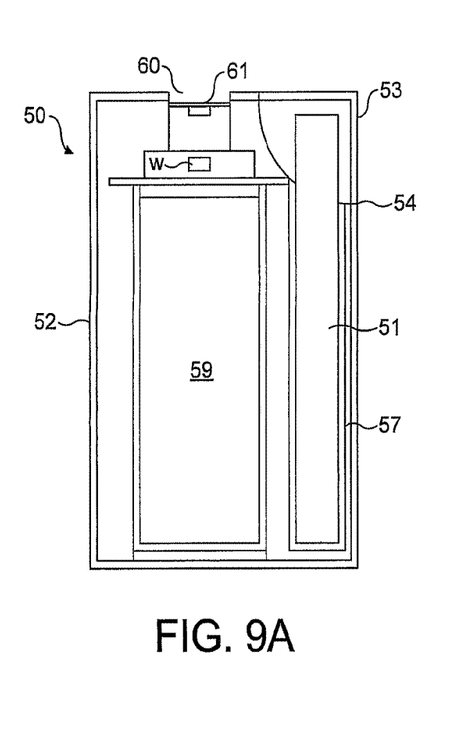
FIG. 9A is a schematic cross-section showing a fourth refill unit with a simulated cigarette device in the stored position.
Figure 9B:
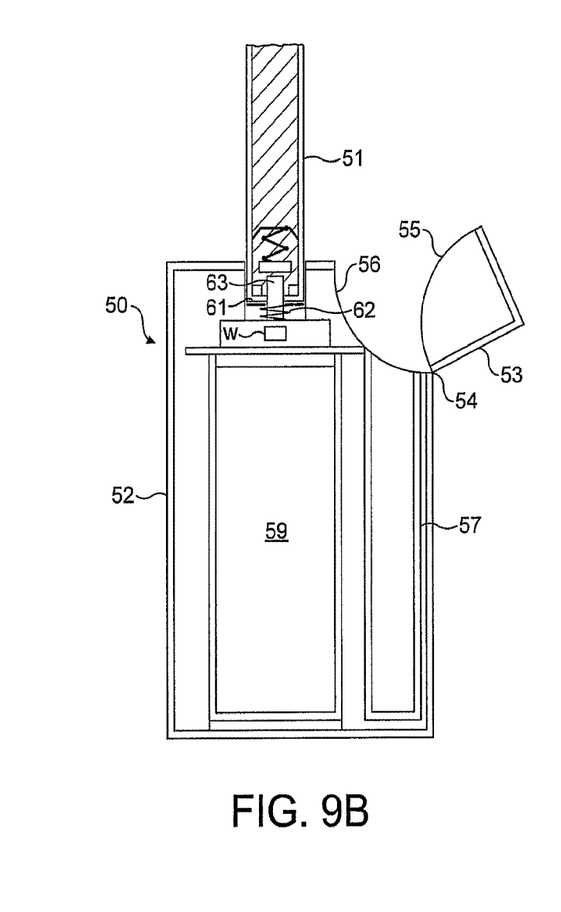
FIG. 9B is a view similar to FIG. 9A, the refill with the simulated cigarette in the refill position.
Figure 10:
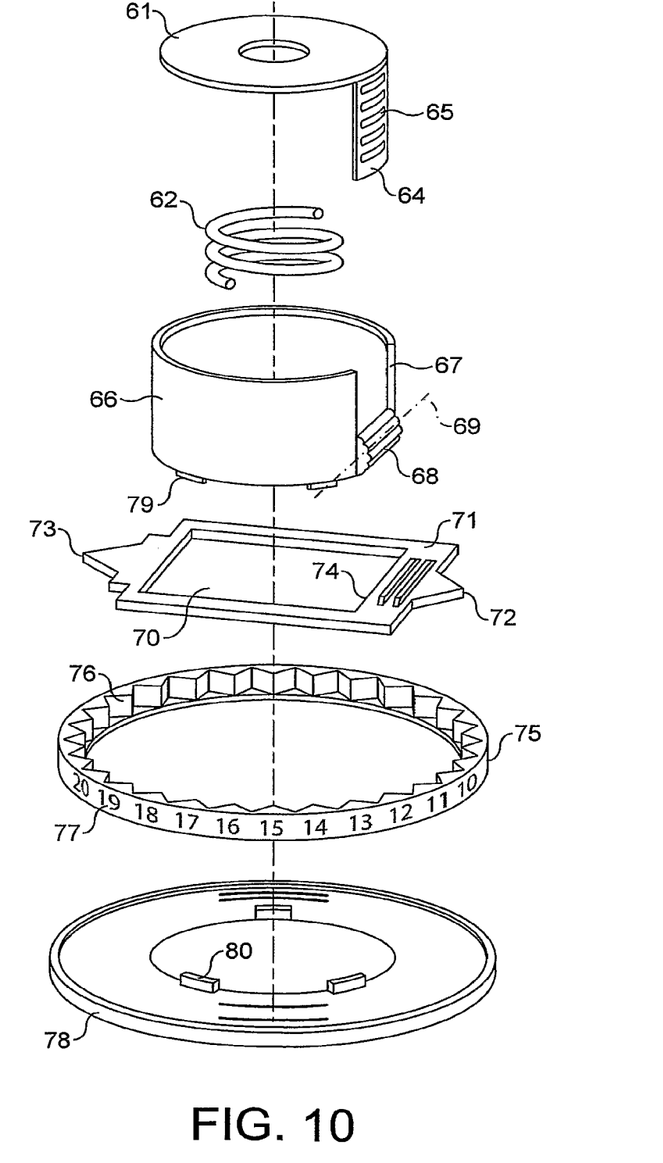
FIG. 10 is an exploded perspective view of a dose counter.
Figure 11A:
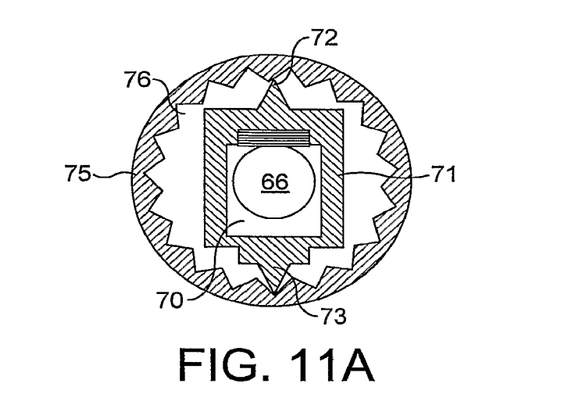
FIGS. 11A-11C are schematic cross-sections through the dose counter in various stages of operation.
Figure 11B:
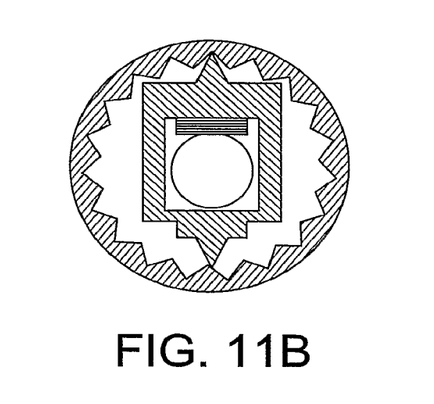
Figure 11C:
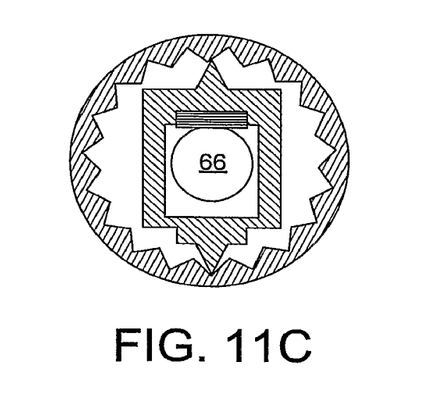

A fourth refill unit 50 and cigarette device 51 are shown in FIGS. 9-11. As with the previous examples, the refill device 50 has a housing 52 which is shaped and dimensioned so as to closely resemble a cigarette pack. The housing 52 has a lid 53 which occupies a corner of the upper portion of the housing. The lid 53 is attached to the housing 52 with a hinge 54 and has an arcuate face 55 which corresponds to a complementary face 56 on the housing 52.

The cigarette device 51 is retained in a recess 57 and is entirely enclosed when the lid 53 is shut as shown in FIG. 9A. The single cylinder 59 is provided within the housing and contains the inhalable composition. The housing 52 has an opening 60 which is the refill aperture. This may be protected by a peel-off membrane to prevent in the ingress of dirt during transportation and storage. A plate 61 is arranged adjacent to the wall of the housing and can be pushed down against the action of a spring 62 to expose a valve stem 63 of the cylinder 59. This allows the cigarette device 51 to be refilled as described above in relation to the earlier examples.

The housing 52 has a window W shown schematically in FIGS. 9A and 9B for a dose counter which is described in more detail in relation to FIGS. 10 and 11 below.

The plate 61 has a depending lip 64 with a plurality of grooves 65. The plate 61 is positioned within a hollow cylindrical housing 66 having a cut-out portion 67 in the bottom of which a gear wheel 68 is mounted to rotate about an axis 69.

The cylindrical housing 66 is positioned within a rectangular opening 70 in slider 71. The slider 71 has a single tooth 72,73 at each end and is arranged such that an inner lip 74 bears against the gear wheel 68. A ring 75 surrounds the slider 70. The ring 75 is provided with a plurality of teeth 76 on its innermost surface and a set of numbers 77 on its outwardly facing surface. All of the components are mounted on a mounting ring 78 such that lugs 79 on the housing 66 mate with corresponding lugs 80 on the mounting ring 78 holding the components in place.

In use as the cigarette device is pressed down on to the plate 61 as shown in FIG. 9B, the lip 64 moves down rotating the gear wheel 68 which moves the ring 75 from the position shown in FIG. 11A to the position shown in FIG. 11B. The tooth 72 on the slider 70 co-operates with a corresponding tooth on the ring 75 thereby rotating the ring 75 slightly in the anticlockwise direction to the position shown in FIG. 11B. Withdrawal of the cigarette device causes the plate 61 to be driven upwardly by the spring 62 such that the lip 64 rotates the wheel 68 in the opposite direction thereby causing the slider to move to the position shown in FIG. 11C in which the tooth 73 moves the ring 75 slightly further in an anticlockwise direction. The combined movement caused by the cigarette device being pushed on to and removed from the plate 61 is sufficient to advance the ring 75 such that the next number in the sequence 77 is displayed in the window 64. This arrangement can therefore provide a count down of the number of doses that remain in the cylinder 59.

Alternative dose counters, for example, which have an electronic mechanism, may be used.

A bag-on-valve system can also be added to the refill canister. A bag-on-value system consists of the aerosol valve with a welded bag. With the bag-on-valve system the compressed air, oxygen, nitrogen or other in the aerosol can is on the outside of the bag and acts as a propellant on the product which is inside the bag. This allows the active ingredients such as nicotine to be separated from the propellant, preferably oxygen, to aid a longer shelf life. The bag-on-valve can be located within the canister and can be supplied by a manufacturer such are EP Spray Systems or Power Container, and can carry the same refilling capability as a standard pressurised canister.

The invention claimed is:
1. A simulated smoking device comprising:
a simulated cigarette; and
a refill device containing refill gas for the simulated cigarette and having a first recess for selectively retaining the simulated cigarette in a first position when the simulated cigarette is not in use and not being refilled, and a second recess for receiving the simulated cigarette in a second position different from the first position to refill the simulated cigarette with the refill gas, the refill device further comprising a dose counter to register, and display to a user, a number of times that the simulated cigarette is refilled.

2. The simulated smoking device according to claim 1, wherein the simulated cigarette has a substantially cylindrical cigarette-like shape and the refill device has a substantially cuboid housing with a cigarette pack-like shape, the first recess for selectively retaining the simulated cigarette being formed in the housing.

3. The simulated smoking device according to claim 2, wherein the simulated cigarette comprises:
    an elongate housing having an inhaling outlet at one end and a refill inlet,
    a reservoir,
    a refill valve adjacent to the refill inlet which is operable to allow gas from the refill device to pass from the refill device into the reservoir, and
    an outlet valve adjacent to the inhaling outlet which is operable to allow gas from the reservoir out of the inhaling outlet.

4. The simulated smoking device according to claim 3, where the refill device comprises:
    a gas reservoir having an outlet and an associated reservoir outlet valve, wherein the refill valve of the simulated cigarette is arranged to co-operate with the reservoir outlet valve to open a flow path from the reservoir of the refill device to the reservoir of the simulated cigarette when the simulated cigarette is inserted into the second recess.

5. A refill device for refilling a simulated cigarette comprising:
    a housing;
    a gas cylinder within the housing containing refill gas for the simulated cigarette;
    a first recess within the housing for selectively retaining the simulated cigarette in a first position when the simulated cigarette is not in use and not being refilled;
    a second recess for receiving the simulated cigarette in a second position different from the first position to refill the simulated cigarette with the refill gas; and
    a counter to register, and display to a user, a number of times that the simulated cigarette is refilled.

6. The refill device according to claim 5, the housing having a substantially cuboid cigarette pack-like shape.

* * * * *